US012714822B2

(12) United States Patent
Sutermeister et al.

(10) Patent No.: US 12,714,822 B2
(45) Date of Patent: Aug. 25, 2026

(54) MULTI-LUMEN CATHETER AND METHOD OF ITS MANUFACTURE

(71) Applicant: St. Jude Medical, Cardiology Division, Inc., St. Paul, MN (US)

(72) Inventors: Derek Sutermeister, Ham Lake, MN (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1143 days.

(21) Appl. No.: 17/621,168

(22) PCT Filed: Jul. 21, 2020

(86) PCT No.: PCT/US2020/042869

§ 371 (c)(1),
(2) Date: Dec. 20, 2021

(87) PCT Pub. No.: WO2021/016235

PCT Pub. Date: Jan. 28, 2021

(65) Prior Publication Data

US 2022/0355068 A1 Nov. 10, 2022

Related U.S. Application Data

(60) Provisional application No. 62/877,499, filed on Jul. 23, 2019.

(51) Int. Cl.
*A61M 25/00* (2006.01)
*A61M 25/01* (2006.01)
(Continued)

(52) U.S. Cl.
CPC .... *A61M 25/0009* (2013.01); *A61M 25/0147* (2013.01); *B29C 35/0805* (2013.01); *B29C 48/0021* (2019.02); *B29C 48/09* (2019.02); *A61M 2025/0036* (2013.01); *A61M 2025/004* (2013.01); *A61M 2025/0047* (2013.01); *B29C 2035/085* (2013.01); *B29K 2071/00* (2013.01); *B29K 2105/0032* (2013.01); *B29L 2031/7542* (2013.01)

(58) Field of Classification Search
CPC .......... A61M 25/0009; A61M 25/0045; B29C 35/0805; B29C 48/0021; B29K 2105/24
See application file for complete search history.

(56) References Cited

U.S. PATENT DOCUMENTS 5,501,694 A 3/1996 Ressemann et al.
5,906,605 A 5/1999 Coxum
(Continued)

OTHER PUBLICATIONS

International Search Report, Written Opinion for International PCT Application No. PCT/US2020/042869 filed Jul. 2020, dated Nov. 23, 2020.
(Continued)

*Primary Examiner* — Rebecca E Eisenberg
(74) *Attorney, Agent, or Firm* — Wiley Rein LLP

(57) ABSTRACT

A catheter assembly is constructed by reflow bonding an inner liner and an outer layer. The inner liner defines at least one lumen. The inner liner is made of a gamma-irradiated polymeric material that includes a polyether block amide and a gamma radiation activated cross-linking agent.

6 Claims, 2 Drawing Sheets

(51) Int. Cl.

| | |
|---|---|
| ***B29C 35/08*** | (2006.01) |
| ***B29C 48/00*** | (2019.01) |
| ***B29C 48/09*** | (2019.01) |
| *B29K 71/00* | (2006.01) |
| *B29K 105/00* | (2006.01) |
| *B29L 31/00* | (2006.01) |

(56) References Cited

U.S. PATENT DOCUMENTS

| | | | | |
|---|---|---|---|---|
| 5,971,975 | A | 10/1999 | Mills et al. | |
| 6,001,438 | A * | 12/1999 | Bourgault | F16L 11/12 428/36.9 |
| 6,217,565 | B1 | 4/2001 | Cohen | |
| 6,582,536 | B2 | 6/2003 | Shimada | |
| 7,037,290 | B2 | 5/2006 | Gardeski et al. | |
| 9,861,433 | B2 | 1/2018 | Tegg | |
| 2002/0058910 | A1 | 5/2002 | Herman et al. | |
| 2004/0236346 | A1 | 11/2004 | Parker | |
| 2007/0060944 | A1 | 3/2007 | Boldenow et al. | |
| 2008/0317791 | A1* | 12/2008 | Trudsoe | A61L 9/012 426/574 |
| 2009/0024110 | A1 | 1/2009 | Heideman et al. | |
| 2009/0224428 | A1* | 9/2009 | Schroeder | A61L 27/50 264/319 |
| 2011/0264057 | A1 | 10/2011 | Eversull et al. | |
| 2014/0142551 | A1 | 5/2014 | Nagata et al. | |
| 2014/0336572 | A1* | 11/2014 | Heisel | A61M 25/0045 604/95.04 |
| 2015/0345689 | A1* | 12/2015 | Selker | F16L 58/185 422/534 |
| 2016/0158491 | A1 | 6/2016 | Pieslak et al. | |
| 2018/0289925 | A1* | 10/2018 | Palmer | A61M 25/0043 |

OTHER PUBLICATIONS

International Search Report, Written Opinion for International PCT Application No. PCT/US08/70287 filed Jul. 17, 2008, dated Nov. 10, 2008.

* cited by examiner 110
100
190
195

MULTI-LUMEN CATHETER AND METHOD OF ITS MANUFACTURE

CROSS-REFERENCE TO RELATED APPLICATIONS

This application claims the benefit of U.S. provisional application No. 62/877,499, filed 23 Jul. 2019, which is hereby incorporated by reference as though fully set forth herein.

BACKGROUND

The present disclosure relates generally to catheters that are used in the human body. In particular, the present disclosure relates to a single- or multi-lumen inner liner for use in catheters, including steerable catheters.

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart.

BRIEF SUMMARY

Disclosed herein is a method of manufacturing a catheter, including the steps of: providing an inner liner defining at least one lumen, wherein the inner liner includes a gamma-irradiated polymeric material, such as a polyether block amide, and a gamma radiation activated cross-linking agent; forming an outer layer over the inner liner; and reflow bonding the outer layer to the inner liner.

In embodiments of the disclosure, the inner liner defines multiple lumens.

The step of providing an inner liner defining at least one lumen can include: extruding the inner liner; and irradiating the extruded inner liner with gamma radiation. According to aspects disclosed herein, the irradiating step occurs substantially simultaneously with the extruding step (e.g., as the extrusion exits the extruder).

The gamma-irradiated polymeric material can also include a colorant and/or a lubricious additive.

It is also contemplated that the method can include installing a steering assembly prior to the reflow bonding step. The steering assembly can include at least one pull wire within the at least one lumen of the inner liner, as well as at least one pull ring around the inner liner.

In still further embodiments of the disclosure, the method can include forming a torque transfer layer about the inner liner prior to the step of forming an outer layer over the inner liner.

Also disclosed herein is a catheter assembly including: an inner liner defining at least one lumen and including a gamma-irradiated polymeric material, such as polyether block amide, and a gamma radiation activated cross-linking agent; and an outer layer reflow bonded to the inner liner.

Embodiments of the catheter assembly disclosed herein can also include a torque transfer layer and/or a steering assembly.

Further, the inner liner can include a colorant and/or a lubricious additive.

The instant disclosure also provides a method of manufacturing a catheter, including: extruding an inner liner defining at least one lumen, wherein the inner liner includes a polymeric material, such as a polyether block amide, and a gamma radiation activated cross-linking agent; exposing the extruded inner liner to gamma radiation, thereby activating the cross-linking agent; inserting at least one steering wire into the at least one lumen; forming an outer layer over the inner liner; and reflow bonding the outer layer to the inner liner.

Optionally, a tip can be attached to a distal end of the extruded inner liner prior to the step of reflow bonding.

The inner liner can include at least one of a colorant and a lubricious additive.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

Figure 1:
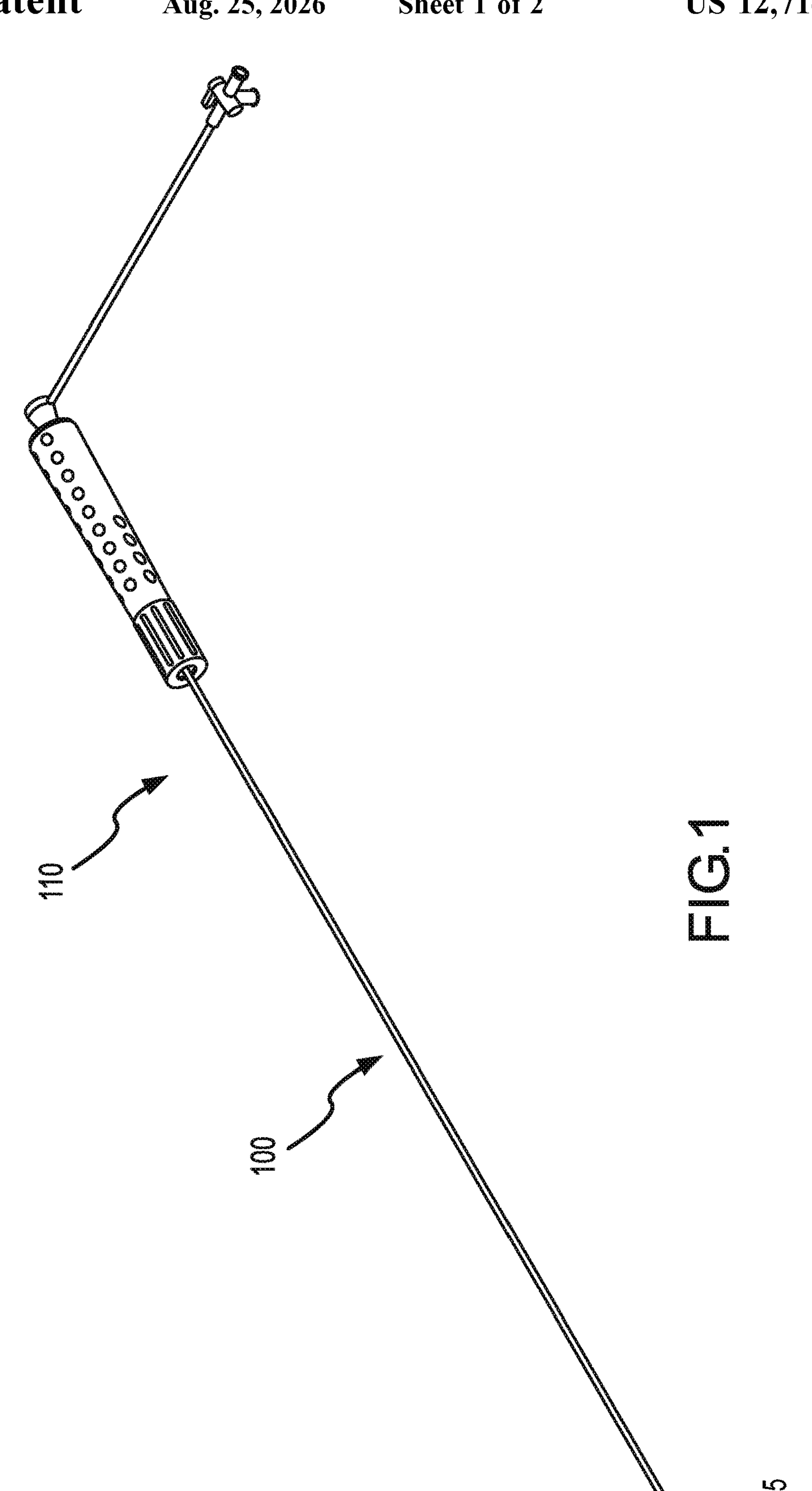
FIG. 1 is a perspective view of a representative catheter according to aspects of the instant disclosure.

FIG. 1 is a perspective view of a catheter 100 according to aspects of the instant disclosure. Catheter 100 has a proximal portion 110 and a distal portion 190.

A basic method of manufacture of catheter 100 according to an embodiment of the instant disclosure will be described with reference to FIGS. 2 and 3. As they are assembled, the various components of catheter 100 will be collectively referred to as a catheter assembly 200.

Figure 2:
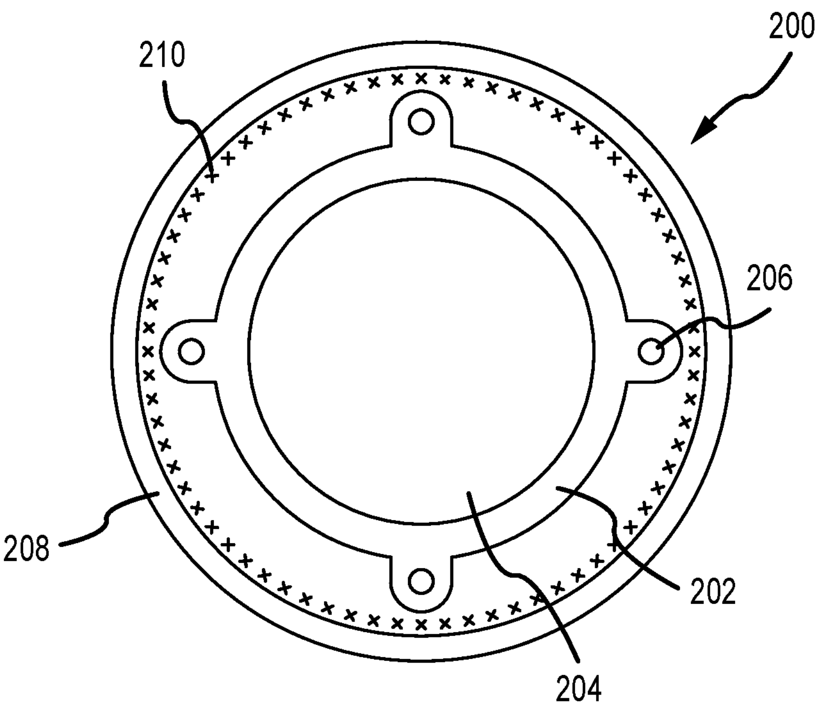
FIG. 2 is a transverse cross-sectional view of a catheter assembly according to aspects of the instant disclosure prior to reflow bonding.

As depicted in FIG. 2, an inner liner 202 is a component of catheter assembly 200 and, in embodiments of the disclosure, may be the first component thereof during manufacture of catheter 100. Inner liner 202 defines at least one lumen; as shown in FIG. 2, inner liner 202 defines a central lumen 204 and four peripheral lumens 206 spaced roughly equally about the circumference of inner liner 202. It should be understood, however, that this configuration is merely illustrative, and other configurations of inner liner 202 are within the scope of the instant disclosure.

Inner liner 202 is made of a gamma-irradiated polymeric material. More particularly, inner liner 202 includes a polyether block amide, such as PEBAX® (Arkema Inc., King of Prussia, PA), and a gamma radiation activated cross-linking agent. In embodiments of the disclosure, inner liner 202 may further include a lubricious additive such as ProPell™ (Foster Corporation, Putnam, CT) and/or a colorant.

According to aspects disclosed herein, inner liner 202 is formed by extruding the gamma-irradiated polymeric material in the desired configuration and exposing the extrusion to gamma radiation. The exposure to gamma radiation results in cross-linking within the material.

In embodiments of the disclosure, the extruded inner liner 202 is exposed to gamma radiation following extrusion (that is, a length of inner liner 202 is extruded, and then the entire length is irradiated). Alternatively, however, the gamma irradiation can occur substantially simultaneously with the extrusion of inner liner 202. For example, a source of gamma radiation can be positioned at the extruder discharge, such that inner liner 202 is irradiated as it exits the extruder. In either case, the irradiated extrusion can be cut to desired lengths for use in the manufacture of catheter 100.

An outer layer 208 is placed over inner liner 202. As will be familiar to those of ordinary skill in the art, outer layer 208 may be made of either single or multiple sections of tubing that may be butted together and/or overlapped with each other.

Optionally, a torque transfer layer 210 may be placed over inner liner 202 before outer layer 208 is applied. As the ordinarily skilled artisan will recognize, torque transfer layer 210 can include a braided wire mesh.

Figure 3:
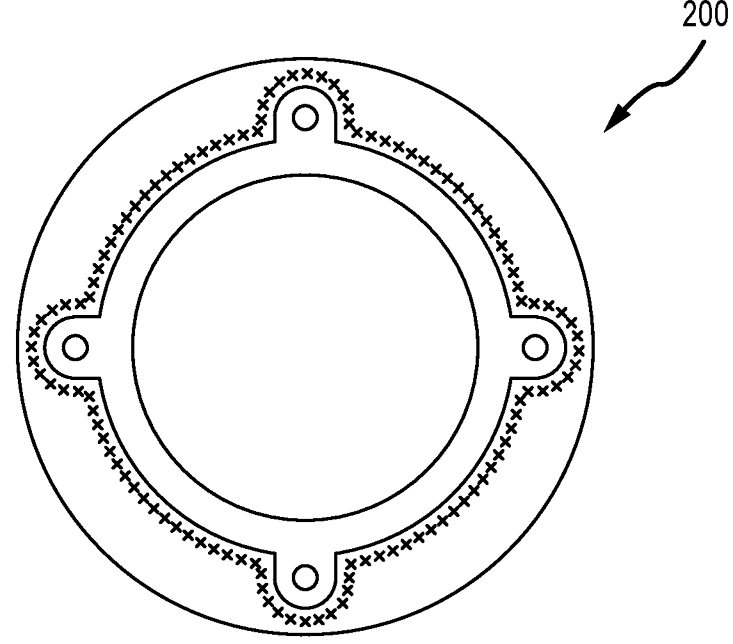
FIG. 3 is a transverse cross-sectional view of a catheter assembly according to aspects of the instant disclosure following reflow bonding.

Outer layer 208 is bonded to inner liner 202 (and torque transfer layer 210, where present) via a lamination process known to those skilled in the art as "reflow bonding." That is, catheter assembly 200 can be laminated by heating it until the material of outer layer 208 flows and redistributes around the circumference of catheter assembly 200 as depicted in FIG. 3. The reflow bonding process can also be facilitated by the inclusion of a heat shrink layer about outer layer 208.

Advantageously, because of the cross-linking, the gamma-irradiated polymeric material of inner liner 202 does not change dimensions during reflow bonding. Thus, the need to insert some sort of instrumentality, such as setup wires, mandrels, or pressurized fluids, to maintain patency of lumens 204 and/or 206 during reflow (and to remove these instrumentalities afterwards) is minimized.

Indeed, instead of setup wires, steering wires (and their associated pull ring(s)) can be added prior to reflow bonding (that is, steering wires can be inserted into lumens 206 prior to reflow bonding). In addition, the tip of catheter 100 can be bonded to distal portion 190 at the same time as outer layer 208 is bonded to inner liner 202. These advantages simplify the manufacture of catheter 100 and reduce its cost relative to extant catheter manufacturing techniques.

Another advantage of using a gamma-irradiated polymeric material for inner liner 202 is that it improves the leak- and aspiration-resistance of catheter 100.

Although several embodiments have been described above with a certain degree of particularity, those skilled in the art could make numerous alterations to the disclosed embodiments without departing from the spirit or scope of this invention.

For example, in addition to steering wires, lumens 206 can be used for irrigant, suction, electrical wires, and the like.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter assembly, comprising:

an inner liner defining at least one lumen and comprising a gamma-irradiated polymeric material and a gamma radiation activated cross-linking agent; and an outer layer reflow bonded to the inner liner.

2. The catheter assembly according to claim 1, wherein the gamma-irradiated polymeric material comprises a gamma-irradiated polyether block amide.

3. The catheter assembly according to claim 1, further comprising a torque transfer layer.

4. The catheter assembly according to claim 1, further comprising a steering assembly.

5. The catheter assembly according to claim 1, wherein the inner liner further comprises a colorant.

6. The catheter assembly according to claim 1, wherein the inner liner further comprises a lubricious additive.

* * * * *